United States Patent [19]
Takeda et al.

[11] Patent Number: 5,012,096
[45] Date of Patent: Apr. 30, 1991

[54] DIGITAL X-RAY APPARATUS

[75] Inventors: Shiro Takeda, Sagamihara; Fumihiro Namiki, Machida; Yuuichi Sugiyama, Chigasaki; Nobuhiro Iwase; Shinji Tadaki, both of Atsugi; Nagaaki Koshino, Yokohama, all of Japan

[73] Assignee: Fujitsu Limited, Kawasaki, Japan

[21] Appl. No.: 525,055

[22] Filed: May 18, 1990

[30] Foreign Application Priority Data

May 20, 1989 [JP] Japan .................................. 1-127583
May 20, 1989 [JP] Japan .................................. 1-127582
Jun. 7, 1989 [JP] Japan .................................. 1-144819

[51] Int. Cl.$^5$ .............................................. G01N 23/03
[52] U.S. Cl. .................................. 250/327.2; 250/484.1
[58] Field of Search ........................... 250/327.2, 484.1

[56] References Cited

U.S. PATENT DOCUMENTS 4,922,100 5/1990 Takeuchi .......................... 250/327.2

Primary Examiner—Carolyn E. Fields
Assistant Examiner—James E. Beyer
Attorney, Agent, or Firm—Staas & Halsey

[57] ABSTRACT

In a digital X-ray apparatus for exposing an X-ray transmitted through an object onto a photostimulable phosphor plate, for scanning the photostimulable phosphor plate by an excitation beam, and for obtaining an X-ray image, the digital X-ray apparatus includes a switch unit connected to a storage unit and switching between a standard photographing mode and an actual photographing mode; a correction coefficient conversion unit converting the X-ray image data to an image data having a standardized lightness; a first storage unit storing an initial correction coefficient after standardization in the correction coefficient conversion unit; a second storage unit storing a correction coefficient after standardization in the correction coefficient conversion unit; a detection unit comparing a value of the correction coefficient from the second storage unit with a value of the initial correction coefficient from the first storage unit, and detecting whether or not a difference between the value of the correction coefficient at each picture element and the value of the initial correction coefficient at each picture element exceeds a predetermined threshold value; and a generation unit displaying a number of abnormal picture elements detected by the detection unit and generating an alarm message when the number of abnormal picture elements exceeds a predetermined number, the predetermined number being defined by a ratio of the number of abnormal picture elements to the number of all the picture elements.

13 Claims, 7 Drawing Sheets

DIGITAL X-RAY APPARATUS

BACKGROUND OF THE INVENTION

1. Field of the Invention

The present invention relates to a X-ray apparatus, more particularly, it relates to a digital X-ray apparatus mainly used in the field of medical equipment.

2. Description of the Related Art

An X-ray apparatus is widely used in various fields, particularly in the medical field. Conventionally, as an X-ray apparatus having high sensitivity and high resolution, there is a digital X-ray apparatus displaying an image on a cathode-ray tube (CRT) instead of a conventional X-ray film.

The digital X-ray image can be obtained by the following steps. That is, when the X-ray is irradiated on to an object, for example, a human body, the X-ray transmitted through the object is exposed on a stimulable phosphor plate constituted by a sheet-like fluorescence medium which is able to accumulate a part of the X-ray energy. When the photostimulable phosphor plate is scanned by an excitation beam (for example, a laser beam), the accumulated energy is excited by the laser beam and a fluorescent light is emitted from the photostimulable phosphor plate.

The fluorescent light is collected by collection equipment, for example, bundled optical fibers, and converted to analog electrical signals by an optical-to-electrical converter. Further, the analog electrical signals are converted to digital signals to obtain the digital X-ray image on the CRT.

Conventionally, however, some problems occur in this method when obtaining the X-ray image. That is, there is deterioration in the characteristics (for example, S/N ratio) of the photostimulable phosphor plate caused by absorption of moisture, and further by damage or dust on the photostimulable phosphor plate and optical device including the laser beam adjuster. This deterioration, causes an abnormal picture on the X-ray image displayed on the CRT which may result in an incorrect diagnosis when an operator evaluates the displayed image.

Accordingly, the most important matter of the digital X-ray apparatus is to increase the precision of the X-ray image so as to prevent incorrect diagnosis caused by abnormal picture elements on the displayed image. Therefore, it is necessary to detect abnormal picture elements before the X-ray apparatus is actually used for diagnosis. Further, it is necessary to display a distribution state of the abnormal picture elements, and to generate an alarm message when the number of the abnormal picture elements exceeds a predetermined threshold level.

SUMMARY OF THE INVENTION

The object of the present invention is to provide a digital X-ray apparatus having high sensitivity, high resolution, and high precision enabling prevention of incorrect diagnosis.

Another object of the present invention is to provide a digital X-ray apparatus having a function which compares an initial state with a use state of the photostimulable phosphor plate, displays the distribution state of the abnormal picture elements, and generates an alarm message when the number of the abnormal picture elements exceeds the predetermined threshold level.

In accordance with the present invention, there is provided a digital X-ray apparatus for exposing an X-ray transmitted through an object to the photostimulable phosphor plate, for scanning the photostimulable phosphor plate by an excitation beam, and for obtaining an X-ray image, the digital X-ray apparatus including: a switch unit connected to a storage unit for switching between a standard photographing mode and an actual photographing mode; a correction coefficient conversion unit for converting the X-ray image data to an image data having a standardized lightness; a first storage unit for storing an initial correction coefficient after standardization in the correction coefficient conversion unit; a second storage unit for storing a correction coefficient after standardization in the correction coefficient conversion unit; a detection unit for comparing a value of the correction coefficient from the second storage unit with a value of the initial correction coefficient from the first storage unit, and for detecting whether or not a difference between the value of the correction coefficient at each picture element and the value of the initial correction coefficient at each picture element exceeds a first predetermined threshold value; and a generation unit for displaying the number of abnormal picture elements detected by the detection unit and for generating an alarm message when the number of abnormal picture elements exceeds the a second predetermined threshold value, the second predetermined threshold value being defined by a ratio of the number of abnormal picture elements to the number of all picture elements.

DESCRIPTION OF THE PREFERRED EMBODIMENTS

Figure 1:
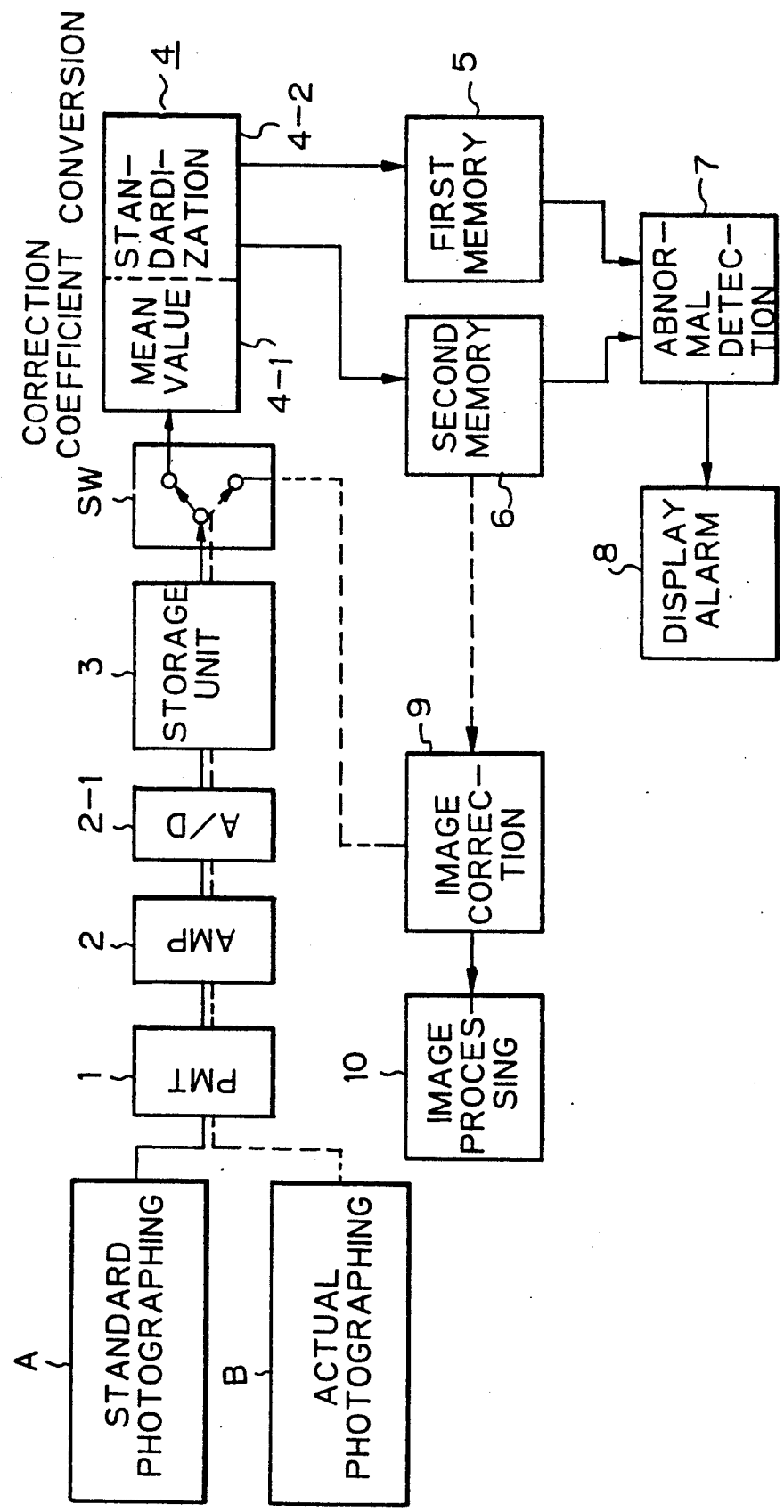
FIG. 1 is a schematic block diagram of a digital X-ray apparatus according to an embodiment of the present invention.

FIG. 1 is a schematic block diagram of an X-ray apparatus according to an embodiment of the present invention. In FIG. 1, reference number 1 denotes an optical-to-electrical converter PMT (photomultiplier), 2 an amplifier AMP, 2-1 an analog-to-digital converter (A/D), 3 a storage unit, 4 a correction coefficient conversion unit, 5 a first memory for storing an initial correction coefficient, 6 a second memory for storing a correction coefficient, 7 a detection unit for detecting abnormal picture elements 8 a generation unit for displaying the number of abnormal picture elements and generating the alarm message, 9 a correction unit for correcting image data, and 10 a processing unit for processing an image. Further, reference letter A denotes image data derived from a standard photographing operation to obtain the image data to the corrected, and B denotes image data derived from an actual photographing operation (routine photographing) to obtain the image data to be corrected in actual use. SW denotes a switch for switching between a solid line for standard photographing and a dotted line for actual photographing. Initially, the switch is connected to the solid line, and after correction, the switch is switched to the dotted line.

The optical-to-electrical converter 1 converts the collected fluorescent light to an electrical signal. Usually, a photomultiplier is used as this converter.

The amplifier 2 amplifies the electrical signal and the output is converted to a digital value by the A/D 2-1.

The storage unit 3 stores the X-ray image data in the form of frame data.

The correction coefficient conversion unit 4 comprises a mean value calculation unit 4-1 and a standardization calculation unit 4-2. The standardization calculation unit 4-2 converts the X-ray image data to an image data having a standardized lightness. The standardized lightness is obtained in such a way that the X-ray image data is divided by a mean value of all picture elements, or a mean value of plural picture elements in the mean value calculation unit 4-1.

The first memory 5 stores the initial correction coefficient after standardization in the unit 4. The initial correction coefficient is obtained in such a way that when an object is not provided, the X-ray is irradiated onto the photostimulable phosphor plate when the plate is changed to a new one. The plate is then scanned by the excitation beam, and the obtained X-ray image is standardized. The standardization is performed by the correction coefficient conversion unit 4.

The second memory 6 stores the correction coefficient after standardization in the unit 4. The correction coefficient is obtained in such a way that when the object is not provided, the X-ray is irradiated onto the photostimulable phosphor plate just before actual use. The plate is then scanned by the excitation beam, and the obtained X-ray image is standardized. The standardization is performed by the correction coefficient conversion unit 4.

The detection unit 7 compares the correction coefficient from the second memory 6 with the correction coefficient from the first memory 5, detects whether or not the difference between the value of the correction coefficient at each picture element and the value of the initial correction coefficient at each picture element exceeds a predetermined threshold value.

The generation unit 8 displays the number of abnormal picture elements from the detection unit 7 and generates the alarm message when the number of abnormal picture elements exceeds a predetermined number. The predetermined number is defined by the ratio of the number of abnormal picture elements to all picture elements (for example, 1% or 0.1%). The operator changes the deteriorated photostimulable phosphor plate to a new one based on the alarm signal.

The correction unit 9 corrects the image data from the storage unit 3 based on the correction coefficient from the correction coefficient memory 6.

The processing unit 10 edits the image data from the correction unit 9 and displays the image data on the display unit.

Figure 2:
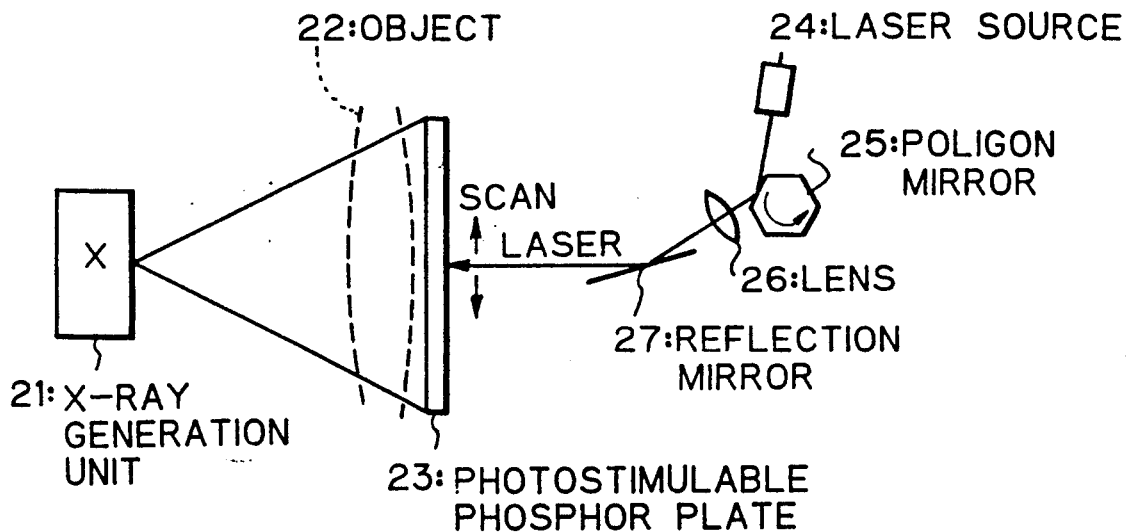
FIG. 2 is a basic structural view of a digital X-ray apparatus applying the present invention.
Figure 3:
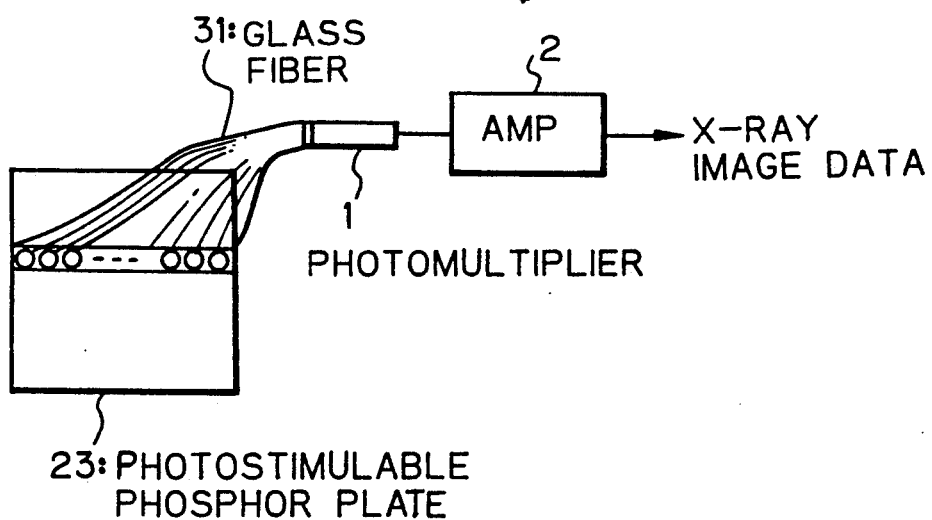
FIG. 3 is a basic structural view for explaining collection of fluorescent light.

FIG. 2 is a basic structural view of an X-ray apparatus applying the present invention, and FIG. 3 is a basic structural view for explaining collection of fluorescent light. In FIG. 2, reference number 21 denotes an X-ray generation unit, 22 an object, 23 a photostimulable phosphor plate, 24 a laser generation unit, 25 a polygon mirror, 26 a lens, and 27 a reflection mirror.

When an X-ray beam having a predetermined energy (for example, 75 kev) is generated from the X-ray generation unit 21 and irradiated onto the object. The X-ray exposes the photostimulable phosphor plate through the object 22. Next, the photostimulable phosphor plate 23 is scanned by the laser beam from the laser generation unit 24 through the polygon mirror 25, the lens 26, and the reflection mirror 27.

In FIG. 3, reference number 31 denotes a collection unit for collecting the fluorescent light generated from the photostimulable phosphor plate 23. The collection unit 31 is made of a glass fiber tube consisting of a plurality of glass fibers. One end of the glass fiber tube 31 is provided for the surface of the photostimulable phosphor plate 23, and the other end of the glass fiber tube 31 is connected to the optical-to-electrical converter 1. The fluorescent light collected by the converter 1 is converted to digital electrical signals. Further, the electrical signals are amplified by the amplifier 2, and the amplifier 2 outputs the X-ray image data.

Figure 4:
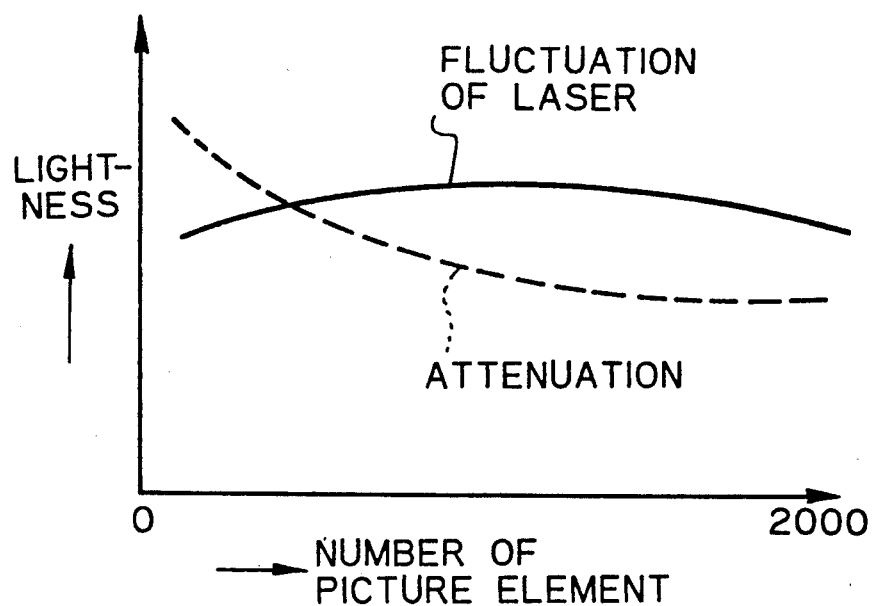
FIG. 4 is a graph for explaining the X-ray image data.

FIG. 4 is a graph for explaining the X-ray image data. The ordinate denotes lightness, and abscissa denotes a number of picture elements per one line. One line means one row of the photostimulable phosphor plate 23 and is constituted by, for example, 2000 picture elements. This graph is for a case where an object is not provided and the exposure is performed under standard conditions. The solid line denotes the change of the lightness of the X-ray image caused by the fluctuation of the output of the laser beam. The dotted line denotes the attenuation of the lightness of the X-ray image. As shown by the graph, the lightness of the X-ray image data per one line is reduced at both ends of one line.

Figure 5:
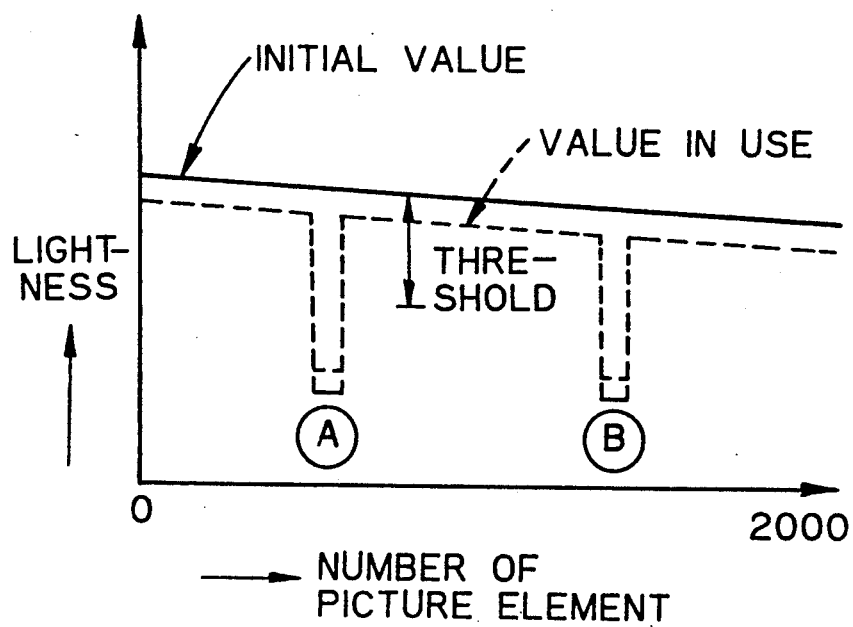
FIG. 5 is a graph for explaining a correction coefficient at each picture element of the X-ray image read out from a frame memory.

FIG. 5 is a graph for explaining the correction coefficient at each picture element of the X-ray image read out from the frame memory. In FIG. 5, the ordinate denotes a standardized lightness and the abscissa denotes a number of picture elements per one line. The solid line denotes the initial value of lightness, and the dotted line denotes the value of lightness in actual use. As shown in the graph, the points A and B are dark points beyond the predetermined threshold level so that these points are determined as abnormal picture elements. These points are displayed on the CRT.

Figure 6:
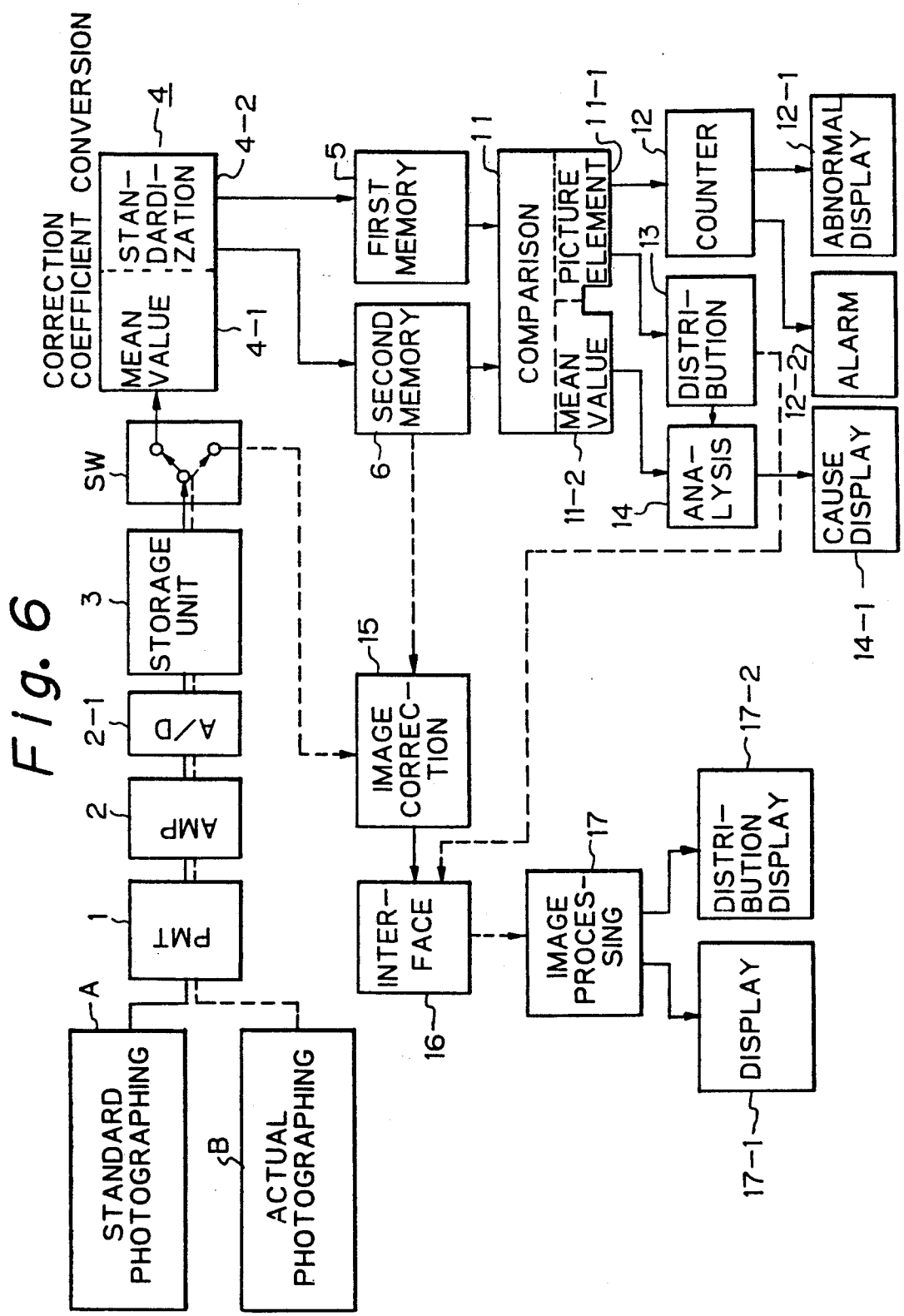
FIG. 6 is a schematic block diagram of the X-ray apparatus according to another embodiment of the present invention.

Further, when the number of abnormal picture elements exceeds 1% of all picture elements, or when the number of abnormal picture elements repeatedly exceeds 0.1% of all picture elements, an alarm message (for example, "change photostimulable phosphor plate") is displayed on the CRT. FIG. 6 is a schematic block diagram of the X-ray apparatus according to another embodiment of the present invention. In FIG. 6, reference number 11 denotes a comparison/calculation unit including a picture element comparison unit 11-1 and a mean value comparison unit 11-2, 12 an abnormal picture element counting unit, 12-1 an abnormal picture element displaying unit, 12-2 an alarm unit, 13 a distribution processing unit for abnormal picture elements, 14 an analyzing unit for determining the cause of abnormal picture elements, 14-1 a display unit for indicating cause and countermeasure, 15 an image data correction unit, 16 an interface, 17 an image processing unit, 17-1 an image display unit, and 17-2 a display unit for abnormal picture elements.

In FIG. 6, the correction coefficient conversion unit 4 comprises the mean value calculation unit 4-1 and the standardization calculation unit 4-2 as in FIG. 1. The picture element comparison unit 11-1 of the comparison/calculation unit 11 compares the value of the correction coefficient of each picture element from the second memory 6 with the value of the correction coefficient of each picture element from the first memory 5, and obtains the distribution of the abnormal elements over the predetermined threshold value. The mean value comparison unit 11-2 compares the mean value of the correction coefficient of each picture element from the second memory 6 with the mean value of the correction coefficient of each picture element from the first memory 5.

The abnormal picture element counting unit 12 counts the number of the abnormal picture elements detected by the picture element comparison unit 11-1. The number of the abnormal picture elements is displayed on the display unit 12-1. Further, the alarm unit 12-2 generates the alarm message.

The distribution processing unit 13 for the abnormal picture elements collects the distribution data of the abnormal picture elements detected by the picture element comparison unit 11-1. The distribution data of the abnormal picture elements is expressed by the matrix address consisting of the column and row, or the head address and the end address of the successive abnormal picture elements in one row.

The analyzing unit 14 analyzes the cause regarding the abnormal picture elements totaling over 1% in all picture elements, or successive abnormal picture elements over 0.1% in all picture elements, and generates the alarm message (for example, "change photostimulable phosphor plate"). This alarm message is displayed on the display unit 14-1.

The image data correction unit 15 corrects the X-ray image data from the storage unit 3 in accordance with the correction coefficient from the second memory 6.

The interface unit 16 transfers the X-ray image data corrected by the correction unit 15 and the distribution data of the abnormal picture elements from the distribution processing unit 13 to the next stage.

The image data processing unit 17 edits the corrected X-ray image data and the distribution data of the abnormal picture elements. The distribution data of the abnormal picture elements is superimposed on the X-ray image data by changing density or color of the abnormal picture elements, and displaying it on the CRT. Further, it is possible to separately display the abnormal picture elements from the X-ray image in one display area.

As explained above, the most important matter of the digital X-ray apparatus is to increase precision of the X-ray image so as to prevent an incorrect diagnosis caused by abnormal picture elements on the displayed image. Therefore, it is necessary to detect abnormal picture elements before the X-ray apparatus is actually utilized for the diagnosis. Further, it is necessary to display a distribution state of the abnormal picture elements, and to generate an alarm signal when the number of the abnormal picture elements exceeds a predetermined threshold level. In the present invention, it is possible to provide an X-ray apparatus having high sensitivity, high resolution, and high precision enabling prevention of wrong diagnosis.

Figure 7:
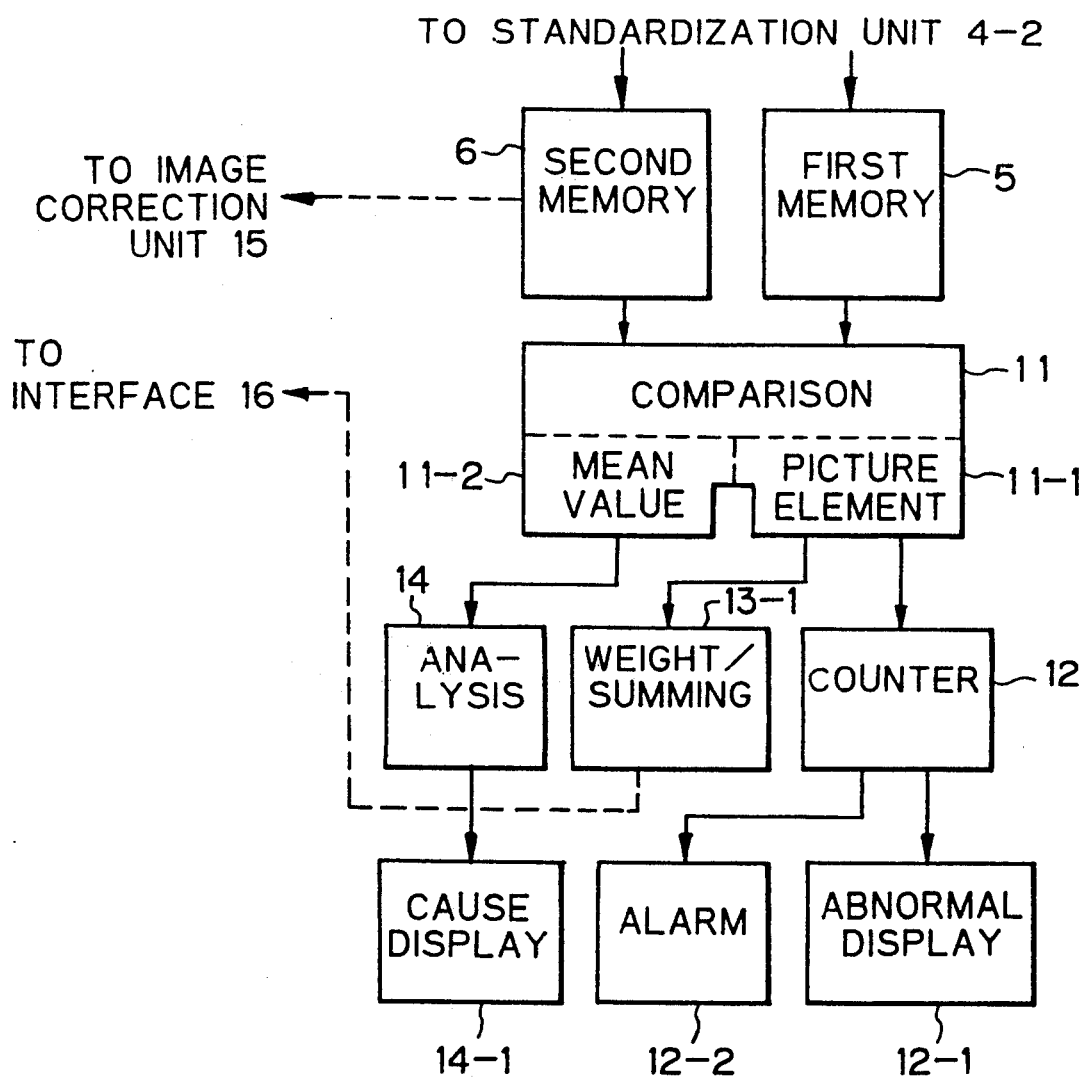
FIG. 7 is a partial schematic block diagram of the X-ray apparatus shown in FIG. 6.

FIG. 7 is a partial schematic block diagram of the X-ray apparatus in still another embodiment shown in FIG. 6. In FIG. 7, reference number 13-1 denotes an abnormal picture elements weighting/summing unit. The abnormal picture elements weighting/summing unit 13-1 inputs the number of the abnormal picture elements detected by the abnormal picture elements counting unit 12 and sums up the number of abnormal picture elements after weighting the number of the picture elements of the adjacent block having the abnormal picture elements. As shown in the drawing, the abnormal picture elements weighting unit 13-1 is connected to the abnormal picture elements counting unit 12 to input the number of the abnormal picture elements. Accordingly, in this embodiment, the grade of the abnormal state is evaluated based on the number of the adjacent abnormal picture elements so that it is possible to detect the abnormal state of the X-ray image.

In this case, the abnormal picture elements weighting/summing unit 13-1 sums the abnormal picture elements in such a way that the number of the abnormal picture elements is counted when they exist discretely on the displayed image, and the number of the picture elements in one block is counted by raising to a second power or fourth power when the plural abnormal picture elements are adjacent.

The second power or fourth power of the number of the abnormal picture elements is used for stressing the abnormal picture elements. In this case, the second power is used when relatively large symptoms are diagnosed, and the fourth power is used when relatively small symptoms are diagnosed.

Figure 8:
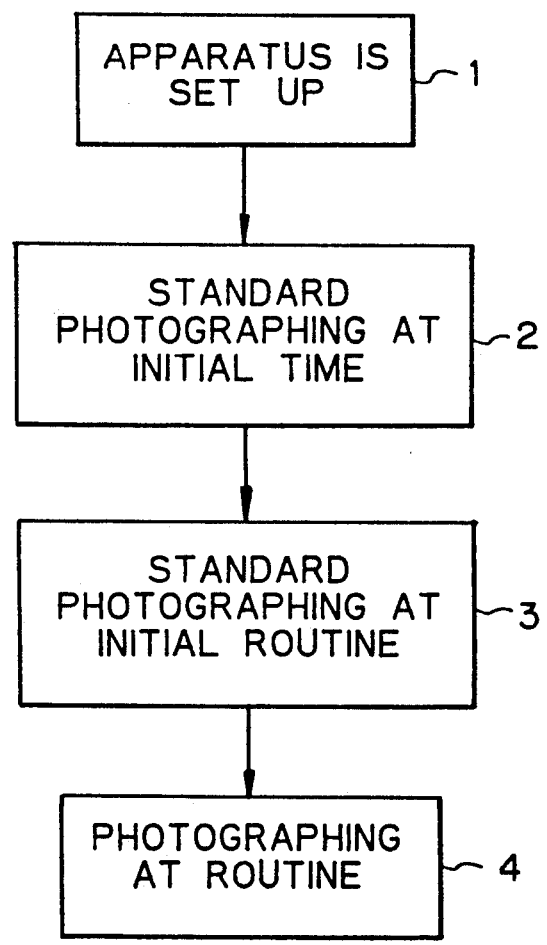
FIG. 8 is a flowchart for explaining basic operation procedures of the present invention.

FIG. 8 is a flowchart for explaining basic operation procedures of the present invention. In the present invention, two photographing operations, i.e., the standard photographing operation A and the actual photographing operation B, are performed to obtain the image data to be corrected as shown in FIGS. 1 and 6. In FIG. 8, when the X-ray apparatus is set up (step 1), the standard photographing operation is performed to detect a change with the passage of time and mechanical and electrical problems with the X-ray apparatus (step 2).

Further, the standard photographing operation is performed to correct the dispersion of the X-ray image during an initial routine before the actual photographing operation is performed (step 3). The correction coefficient can be obtained after the above steps, and the actual photographing operation, i.e., routine photographing, is automatically performed (step 4). In this case, the initial state means the time when the X-ray tube, the photostimulable phosphor plate, or the part is changed to a new one.

Figure 9:
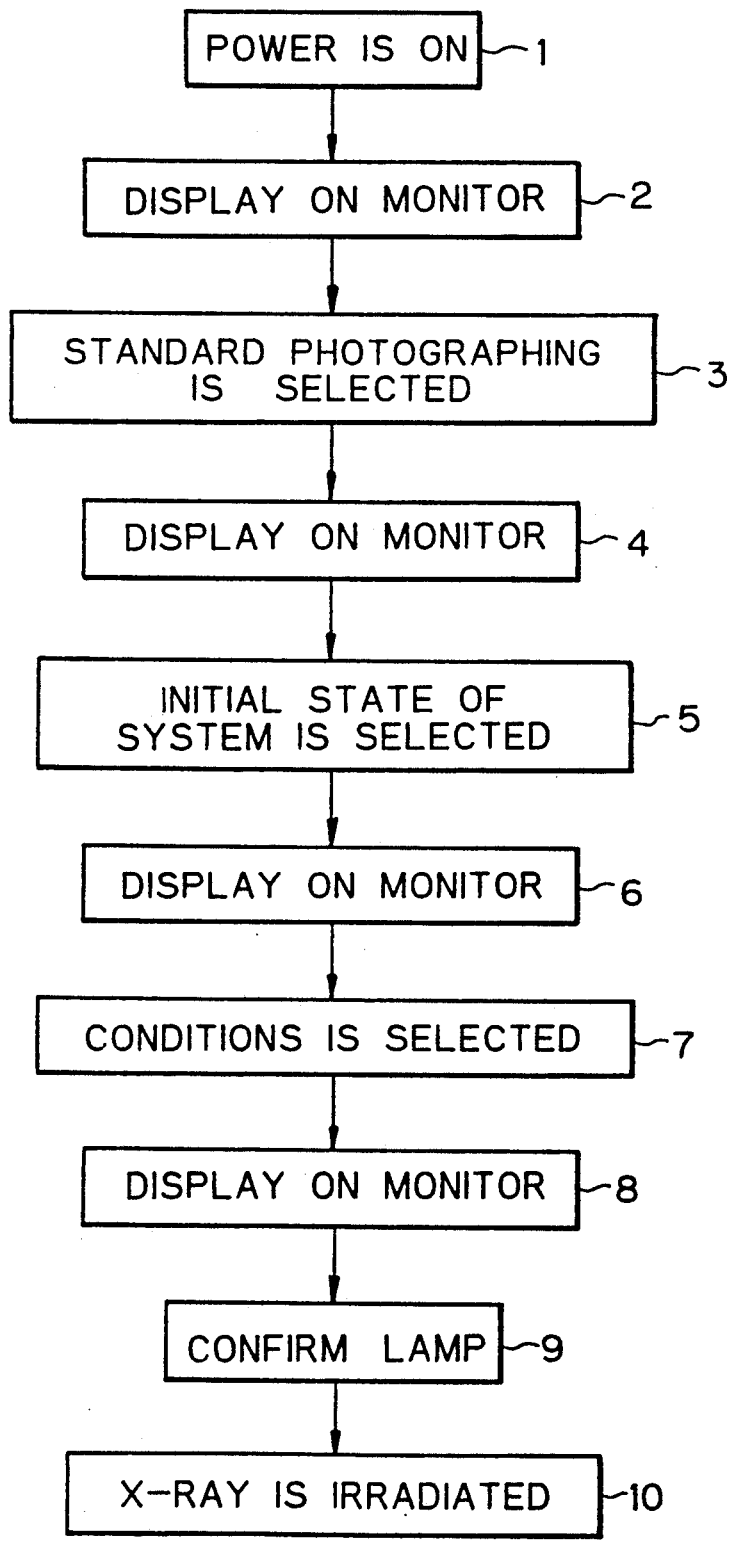
FIG. 9 is a detailed flowchart for explaining the standard photographing shown in FIG. 8.

FIG. 9 is a detailed flowchart for explaining the standard photographing operation shown in FIG. 8. In FIG. 9, when the power of the X-ray apparatus is turned ON (step 1) four modes (standard photographing mode, automatic photographing mode, photographing conditions setting mode, and content of disk displaying mode) are displayed on the monitor (step 2) and the operator selects the standard photographing mode (step 3). When the standard photographing mode including "initial state of system" and "initial state of routine" is displayed on the monitor (step 4), the initial state of system is selected (step 5).

When the initial state of system is selected, the various conditions of the standard photographing operation, for example, distance between the X-ray tube and the object, voltage of the X-ray tube, irradiation time, etc., are displayed on the monitor (step 6) and the operator determines each condition (step 7). Further, the standard photographing operation including "routine mode" and "histogram mode" is displayed on the monitor (step 8), the operator confirms a blue lamp indicating the go-sign (step 9) and the X-ray is irradiated onto the object. There are two modes in the histogram, i.e., a read data histogram and a correction coefficient histogram. In the read data histogram, the ordinate denotes the frequency of the data and the abscissa denotes the digital value. In the correction coefficient histogram, the ordinate denotes the frequency of the data and the abscissa denotes the correction coefficient.

The standard photographing operation at the "initial state of routine" is performed by the same steps as above except that the "initial state of routine" mode is selected in step 4 of FIG. 9.

The many features and advantages of the invention are apparent from the detailed specification and thus it is intended by the appended claims to cover all such features and advantages of the invention which fall within the true spirit and scope thereof. Further, since numerous modifications and changes will readily occur to those skilled in the art, it is not desired to limit the invention to the exact construction and operation illustrated and described, and accordingly all suitable modifications and equivalents may be restored to as falling within the scope of the invention.

What is claimed is:

1. A digital X-ray apparatus for exposing X-rays transmitted through an object to a photostimulable phosphor plate, for scanning the photostimulable phosphor plate by an excitation beam to produce X-ray image data, and for obtaining an X-ray image, said digital X-ray apparatus comprising:
    switch means for switching between a standard photographing mode and an actual photographing mode;
    correction coefficient conversion means for converting the X-ray image data to image data having a standardized lightness;
    first storage means for storing an initial correction coefficient after standardization in said correction coefficient conversion means;
    second storage means for storing a current correction coefficient after standardization in said correction coefficient conversion means;
    detection means for comparing a value of the current correction coefficient from said second storage means with a value of the initial correction coefficient from said first storage means, and for detecting whether or not a difference between the value of the current correction coefficient at each picture element and the value of the initial correction coefficient at each picture element exceeds a predetermined threshold value; and
    generation means for displaying a number of abnormal picture elements detected by said detection means and for generating an alarm message when the number of abnormal picture elements exceeds a predetermined number, the predetermined number being defined by a ratio of the number of abnormal picture elements to a number of all the picture elements.

2. A digital X-ray apparatus as claimed in claim 1, wherein said correction coefficient conversion means comprises a mean value calculation unit and a standardization calculation unit operatively connected to said mean value calculation unit, and
    wherein the image data having standardized lightness is obtained by said standardization calculation unit in such a way that the X-ray image data is divided by one of a mean value of all picture elements and a mean value of plural picture elements.

3. A digital X-ray apparatus as claimed in claim 1, comprising means to determine the initial correction coefficient in such a way that when the object is not provided, the X-ray is irradiated onto the photostimulable phosphor plate; the photostimulable phosphor plate is scanned by the excitation beam, and the X-ray image obtained is standardized.

4. A digital X-ray apparatus as claimed in claim 1, comprising means to determine the current correction coefficient in such a way that when the object is not provided, the X-ray is irradiated onto the photostimulable phosphor plate just before actual use, the photostimulable phosphor plate is scanned by the excitation beam, and the X-ray image obtained is standardized.

5. A digital X-ray apparatus for exposing X-rays transmitted through an object to a photostimulable phosphor plate, for scanning the photostimulable phosphor plate by an excitation beam to produce X-ray image data, and for obtaining an X-ray image, said digital X-ray apparatus comprising:
    switch means for switching between a standard photographing mode and an actual photographing mode;
    correction coefficient conversion means for converting the X-ray image data to image data having a standardized lightness;
    first storage means for storing an initial correction coefficient after standardization in said correction coefficient conversion means;
    second storage means for storing a current correction coefficient after standardization in said correction coefficient conversion means;
    comparison/calculation means including at least
        picture element comparison means for comparing a value of the current correction coefficient of each picture element from said second storage means with a value of the initial correction coefficient of each picture element from said first storage means and for obtaining a distribution of the abnormal picture elements over a predetermined threshold value, and
        mean value comparison unit means for comparing a mean value of the initial correction coefficient of each picture element from said second storage means with a mean value of the initial correction coefficient of each picture element from said first storage means;
    abnormal picture element counting means for counting a number of the abnormal picture elements, said abnormal picture element counting means including at least
    abnormal picture element displaying means for displaying the number of the abnormal picture elements, and
    alarm means for generating an alarm message;

distribution processing means for collecting the abnormal picture elements and obtaining distribution data thereof; and analyzing means for analyzing the abnormal picture elements to determine a cause and for displaying the cause and a countermeasure.

6. An X-ray apparatus as claimed in claim 5, wherein said distribution processing means comprises abnormal picture elements weighting/summing means for inputting the number of the abnormal picture elements detected by said abnormal picture element counting means and for summing up the number of abnormal picture elements after weighting the number of the abnormal picture elements of an adjacent block having the abnormal picture elements.

7. A method for producing an improved X-ray image of an object using a photostimulable phosphor plate having a surface, said method comprising the steps of:
(a) receiving initial X-ray image data of the surface of the photostimulable phosphor plate without the presence of the object;
(b) converting the initial X-ray image data into standardized initial data by standardizing the initial X-ray image data;
(c) receiving current X-ray image data of the surface of the photostimulable phosphor plate without the presence of the object;
(d) converting the current X-ray image data into standardized current data by standardizing the current X-ray image data;
(e) comparing the standardized initial data and the standardized current data; and
(f) identifying abnormal picture elements based on said comparing in step (e).

8. A method as claimed in claim 7,
wherein the standardized current data and the standardized initial data include a plurality of picture elements,
wherein said comparing step (e) comprises the steps of:

(e1) determining a difference between the standardized current data and the standardized initial data for each of the picture elements; and
(e2) comparing the difference with a predetermined threshold value, and
wherein said identifying in step (f) identifies an abnormal picture element when said comparing in step (e2) indicates the difference exceeds the predetermined threshold value.

9. A method as claimed in claim 8,
wherein said identifying in step (f) includes the step of counting a number of the abnormal picture elements, and
wherein said method comprises the step of (g) generating an alarm message based on the number of the abnormal picture elements.

10. A method as claimed in claim 9, wherein said method further comprises the steps of:
(h) receiving object X-ray image data of the surface of the photostimulable phosphor plate with the presence of the object; and
(i) correcting the object X-ray image data using the current X-ray image data to produce corrected X-ray image data.

11. A method as claimed in claim 10, wherein said method further comprises the steps of:
(j) displaying the corrected X-ray image data; and
(k) distinguishably displaying the abnormal picture elements.

12. A method as claimed in claim 7, wherein said method further comprises the steps of:
(g) receiving object X-ray image data of the surface of the photostimulable phosphor plate with the presence of the object; and
(h) correcting the object X-ray image data using the current X-ray image data to produce corrected X-ray image data.

13. A method as claimed in claim 12, wherein said method further comprises the steps of:
(i) displaying the corrected X-ray image data; and
(j) distinguishably displaying the abnormal picture elements.

* * * * *

UNITED STATES PATENT AND TRADEMARK OFFICE
CERTIFICATE OF CORRECTION

PATENT NO. : 5,012,096
DATED : April 30, 1991
INVENTOR(S) : Shiro Takeda et al.

It is certified that error appears in the above-identified patent and that said Letters Patent is hereby corrected as shown below:

Front Page [75] Inventors, line 2, "Machida" s/b --Atsugi--.

Col. 1, line 6, "a X-ray" s/b --an X-ray--.

Col. 7, line 33, "restored" s/b --resorted--.

Col. 8, line 17, "plate;" s/b --plate,--.

Signed and Sealed this

Twenty-fourth Day of November, 1992

*Attest:*

DOUGLAS B. COMER

*Attesting Officer*      *Acting Commissioner of Patents and Trademarks*